United States Patent [19]

Dacons

[11] 4,260,837

[45] Apr. 7, 1981

[54] RECRYSTALLIZATION OF HEXSANITROSTILBENE FROM NITRIC ACID AND WATER

[75] Inventor: Joseph C. Dacons, Washington, D.C.

[73] Assignee: The United States of America as represented by the Secretary of the Navy, Washington, D.C.

[21] Appl. No.: 126,269

[22] Filed: Mar. 3, 1980

[51] Int. Cl.$^3$ ............................................. C07C 79/10
[52] U.S. Cl. ................................................... 568/931
[58] Field of Search ........................................ 568/931

[56] References Cited

U.S. PATENT DOCUMENTS

| | | | |
|---|---|---|---|
| 3,201,481 | 8/1965 | Catino et al. | 568/931 |
| 3,505,413 | 4/1970 | Shipp | 568/931 |
| 3,699,176 | 10/1972 | Syrop | 568/931 |
| 4,085,152 | 4/1978 | Salter et al. | 568/931 |

FOREIGN PATENT DOCUMENTS 2256144  7/1975  France ..................... 568/931

OTHER PUBLICATIONS

O'Keefe, Chem. Abs., vol. 87, 186685h (1977).

*Primary Examiner*—Leland A. Sebastian
*Attorney, Agent, or Firm*—R. S. Sciascia; A. L. Branning; R. D. Johnson

[57] ABSTRACT

The production of 2,2',4,4',6,6'-hexanitrostilbene-I (HNS-I) having finely divided particles of uniform size by dissolving HNS-II in hot fuming nitric acid and then drowning the HNS-nitric acid solution in water.

9 Claims, No Drawings

RECRYSTALLIZATION OF HEXSANITROSTILBENE FROM NITRIC ACID AND WATER

BACKGROUND OF THE INVENTION

This invention relates to aromatic compounds and more particularly to aromatic compounds containing nitro groups.

HNS-I is used in explosive actuating devices, detonating cords, flexible shape charges, etc. The HNS-I which is produce by conventional processes is crude and therefore has a low thermal stability. Washing the crude product with solvents only removes the surface contaminants; impurities which have cocrystallized or occluded with the product HNS-I are not removed. Another method of purification is to dissolve the crude HNS-I in hot fuming nitric acid and then allow the solution to slowly cool to room temperature. This method produces pure HNS-II. (HNS-II differs from HNS-I primary in that HNS-II has a significantly larger particle size.) Because of its larger particle size, HNS-II is less suitable for use in applications such as detonation cords or flexible shape charges. In devices such as these, particle size is so important that impure HNS-I is frequently used instead of pure HNS-II. Yet another approach is to digest the crude HNS-I by heating it in organic solvents; however, crystal growth occurs during this procedure and a wide particle size distribution results. There have been a variety of situations where pyrotechnic devices loaded with this treated HNS-I have failed because of faulty loading caused by the unusually wide particle size distribution.

SUMMARY OF THE INVENTION

Accordingly, an object of the present invention is to provide a new method of recrystallizing 2,2',4,4',6,6'-hexanitrostilbene (HNS).

Another object of this invention is to provide high purity, finely divided HNS-I having a uniform particle size.

Another object of this invention is to provide a method of producing a form of HNS which is suitable for use in detonating cords, flexible shape charges, and other flexible explosive devices.

These and other objectives of this invention are accomplished by providing a process for producing finely divide 2,2',4,4',6,6'-hexanitrostilbene-I (HNS-I) of uniform particle size comprising:

(1) dissolving an explosive material selected from the group consisting of (a) crude HNS-I, (b) purified HNS-I having a wide range of particle sizes, and (c) purified HNS-II in hot fuming nitric acid; and then (2) drowning the HNS/fuming nitric acid solution in water;

provided that the ratio of $HNO_3$ to water is from 1:9 to 4:1 in the final mixture resulting from step (2).

DETAILED DESCRIPTION OF THE PREFERRED EMBODIMENT 2,2',4,4',6,6'-hexanitrostilbene (HNS) is available as crude HNS-I, crude HNS-I which has been digested or recrystallized to form purer HNS-I having a wide range of particle sizes, and pure HNS-II. The present process is used to convert these materials to finely divide HNS-I particles of more uniform size. The process does little to remove impurities from the HNS. Therefore, preferably digested or recrystallized HNS-I or pure HNS-II should be used. The process is more preferably used to convert HNS-II (high purity HNS of large particle size) to HNS-I.

The HNS is first dissolved in hot fuming (90%) nitric acid. Other solvents such as organic solvents or other inorganic acids are not used because of the poor solubility of HNS in them. Moreover, fuming nitric acid is used because as the water content of the acid is increased the solubility of HNS is greatly reduced.

In the second step the hot HNS-fuming nitric acid solution is drowned in water. The HNS-fuming nitric acid solution is added carefully to the water with constant agitation (e.g., stirring) of the mixture. It is also preferable to cool the mixture during this step to prevent overheating. The ratio of $HNO_3$ to water in the final mixture is from 1:9 to 7:3, preferably from 2:1 to 1:2, and more preferably from 1:1.2 to 1.25:1.

The general nature of the invention having been set forth, the following examples are presented as specific examples thereof. It will be understood that the invention is not limited to these specific examples but is suceptible to various modifications that will be recognized by one of ordinary skill in the art.

EXAMPLE 1

A 20 g sample of 2,2', 4,4',6,6'-hexanitrostilbene-I (HNS-I), mp 314°–315° C., was dissolved in 400 ml of hot 90% nitric acid and filtered with suction (while still hot) into a flask containing 400 ml of ice and water. Stirring was continued until flask was cool. The product was recovered by filtration and dried. The recovered product was 19.6 g of very fine uniformly crystalline HNS, mp 314°–315° C., which was distinctly in the HNS-I particle size range.

EXAMPLE 2

A sample of 2,2',4,4',6,6'-hexanitrostilbene-II (HNS-II) was recrystallized using the procedure of example 1. The particle size of the resulting product was essentially identical to that obtained in example 1 (HNS-I size) but the melting point was 318°–319° C., indicating a very high purity. Again the particle size was uniform.

Dilute nitric acid solutions, rather than water, were also tried as drowning media. Drowning solutions were varied so as to give final acid concentrations of 50%, 70% and 80% nitric acid.

Obviously, numerous modifications and variations of the present invention are possible in light of the above teaching. It is therefore to be understood that within the scope of the appended claims the invention may be practiced otherwise than as specifically described herein.

What is claimed as new and desired to be secured by Letters Patent of the United States is:

1. A process for producing finely divided 2,2',4,4',6,6'-hexanitrostilbene-I (HNS-I) of uniform particle size comprising:

(1) dissolving 2,2',4,4',6,6'-hexanitrostilbene-II in hot fuming nitric acid; and then (2) drowning the fuming nitric acid solution in water; provided that the ratio of $HNO_3$ to water is from 1:9 to 4:1 in the final mixture resulting from step (2).

2. The process of claim 1 wherein the ratio of $HNO_3$ to water is from 1:2 to 2:1 in the final mixture resulting from step (2).

3. The process of claim 1 wherein the ratio of HNO₃ to water is from 1:1.2 to 1.25:1 in the final mixture resulting from step (2).

4. A process for producing finely divided 2,2',4,4',6,6'-hexanitrostilbene-I (HNS-I) of uniform particle size comprising:
   (1) dissolving 2,2',4,4',6,6'-hexanitrostilbene-I having a wide range of particle sizes in hot fuming nitric acid; and then
   (2) drowning the fuming nitric acid solution in water; provided that the ratio of HNO₃ to water is from 1:9 to 4:1 in the final mixture resulting from step (2).

5. The process of claim 4 wherein the ratio of HNO₃ to water is from 1:2 to 2:1 in the final mixture resulting from step (2).

6. The process of claim 4 wherein the ratio of HNO₃ to water is from 1:1.2 to 1.25:1 in the final mixture resulting from step (2).

7. A process for producing finely divided 2,2',4,4',6,6'-hexanitrostilbene-I (HNS-I) of uniform particle size comprising:
   (1) dissolving crude 2,2',4,4',6,6'-hexanitrostilbene-I in hot fuming nitric acid; and then
   (2) drowning the fuming nitric acid solution in water; provided that the ratio of HNO₃ to water is from 1:9 to 4:1 in the final mixture resulting from step 2.

8. The process of claim 7 wherein the ratio of HNO₃ to water is from 1:2 to 2:1 in the final mixture resulting from step (2).

9. The process of claim 7 wherein the ratio of HNO₃ to water is from 1:1.2 to 1.25:1 in the final mixture resulting from step (2).

* * * * *